US009204828B2

(12) United States Patent
Burnett et al.

(10) Patent No.: US 9,204,828 B2
(45) Date of Patent: Dec. 8, 2015

(54) CONTINUOUS BLOOD GLUCOSE MONITOR

(75) Inventors: Daniel Rogers Burnett, San Francisco, CA (US); Alejandro Covalin, Culver City, CA (US)

(73) Assignee: TheraNova, LLC, San Francisco, CA (US)

( * ) Notice: Subject to any disclaimer, the term of this patent is extended or adjusted under 35 U.S.C. 154(b) by 0 days.

(21) Appl. No.: 13/306,335

(22) Filed: Nov. 29, 2011

(65) Prior Publication Data
US 2012/0165641 A1 Jun. 28, 2012

Related U.S. Application Data

(63) Continuation of application No. PCT/US2010/036950, filed on Jun. 1, 2010.

(60) Provisional application No. 61/217,537, filed on Jun. 1, 2009, provisional application No. 61/337,648, filed on Feb. 11, 2010.

(51) Int. Cl.
*A61B 5/00* (2006.01)
*A61B 5/145* (2006.01)
*A61B 5/1455* (2006.01)
*A61B 5/1459* (2006.01)
*A61B 5/1473* (2006.01)
*A61B 5/1486* (2006.01)

(52) U.S. Cl.
CPC ............ *A61B 5/14532* (2013.01); *A61B 5/1455* (2013.01); *A61B 5/1459* (2013.01); *A61B 5/1473* (2013.01); *A61B 5/14865* (2013.01); *A61B 5/4839* (2013.01)

(58) Field of Classification Search
CPC . A61B 5/14532; A61B 5/4839; A61B 5/1455
USPC ......................................... 600/345, 347, 365
See application file for complete search history.

(56) References Cited

U.S. PATENT DOCUMENTS

| 2,849,002 | A | 8/1958 | Oddo | |
|---|---|---|---|---|
| 5,484,384 | A | 1/1996 | Fearnot | |
| 6,575,932 | B1 | 6/2003 | O'Brien et al. | |
| 7,727,147 | B1 * | 6/2010 | Osorio et al. | 600/365 |
| 2002/0068860 | A1 * | 6/2002 | Clark, Jr. | 600/347 |
| 2003/0125613 | A1 * | 7/2003 | Enegren et al. | 600/347 |
| 2005/0065556 | A1 | 3/2005 | Reghabi et al. | |
| 2005/0107855 | A1 | 5/2005 | Lennox et al. | |
| 2007/0203396 | A1 | 8/2007 | McCutcheon et al. | |
| 2007/0237739 | A1 | 10/2007 | Doty | |
| 2008/0086042 | A1 * | 4/2008 | Brister et al. | 600/347 |
| 2008/0097468 | A1 | 4/2008 | Adams et al. | |
| 2008/0097469 | A1 | 4/2008 | Gruber et al. | |

(Continued)

FOREIGN PATENT DOCUMENTS

WO    WO 92/13271    8/1992
WO    WO 2010/141503    12/2010

*Primary Examiner* — Navin Natnithithadha
*Assistant Examiner* — Christian Jang
(74) *Attorney, Agent, or Firm* — Levine Bagade Han LLP

(57) ABSTRACT

A device may be implanted subcutaneously with an attached catheter inserted within, e.g., the peritoneal cavity of a subject. The catheter and/or device may also be inserted into another space, e.g., subcutaneous, vascular, peritoneal, cerebrospinal, pleural spaces, etc. The peritoneal fluid which normally collects and/or flows through the peritoneal cavity may be detected by the catheter and analyzed via the device to detect the concentration of glucose within the fluid.

25 Claims, 6 Drawing Sheets

(56) References Cited

U.S. PATENT DOCUMENTS

| | | |
|---|---|---|
| 2008/0097471 A1 | 4/2008 | Adams et al. |
| 2008/0245371 A1 | 10/2008 | Gruber |
| 2008/0300571 A1 | 12/2008 | LePivert |
| 2009/0018424 A1 | 1/2009 | Kamath et al. |
| 2009/0076573 A1 | 3/2009 | Burnett et al. |
| 2010/0087798 A1 | 4/2010 | Adams et al. |
| 2011/0054488 A1 | 3/2011 | Gruber et al. |
| 2012/0136343 A1 | 5/2012 | Burnett |
| 2012/0310269 A1 | 12/2012 | Fearnot et al. |
| 2013/0072786 A1 | 3/2013 | Keogh et al. |
| 2014/0107404 A1 | 4/2014 | Gruber |

* cited by examiner

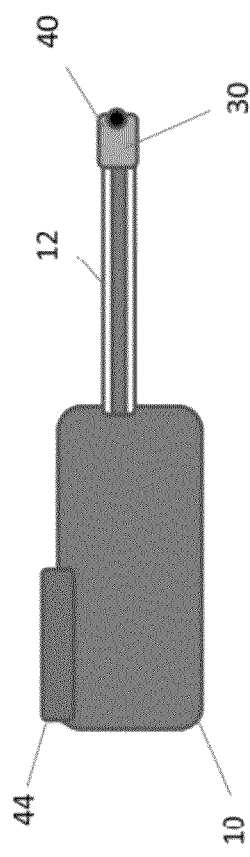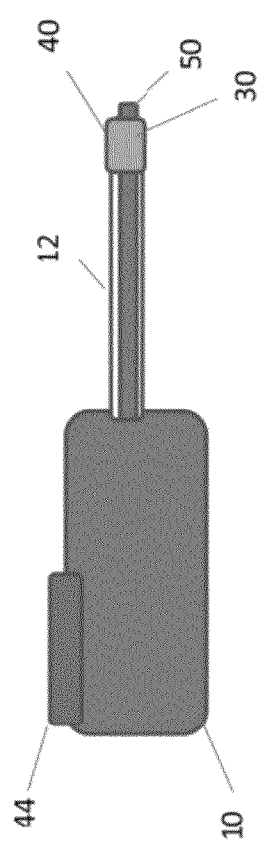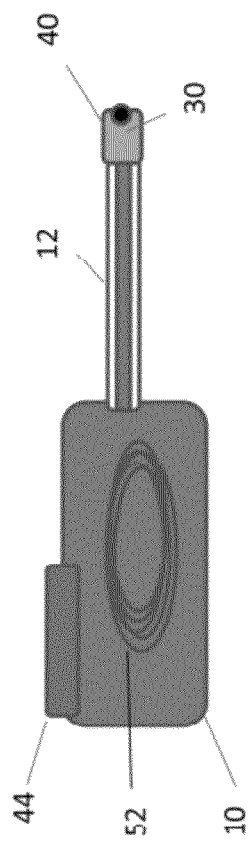

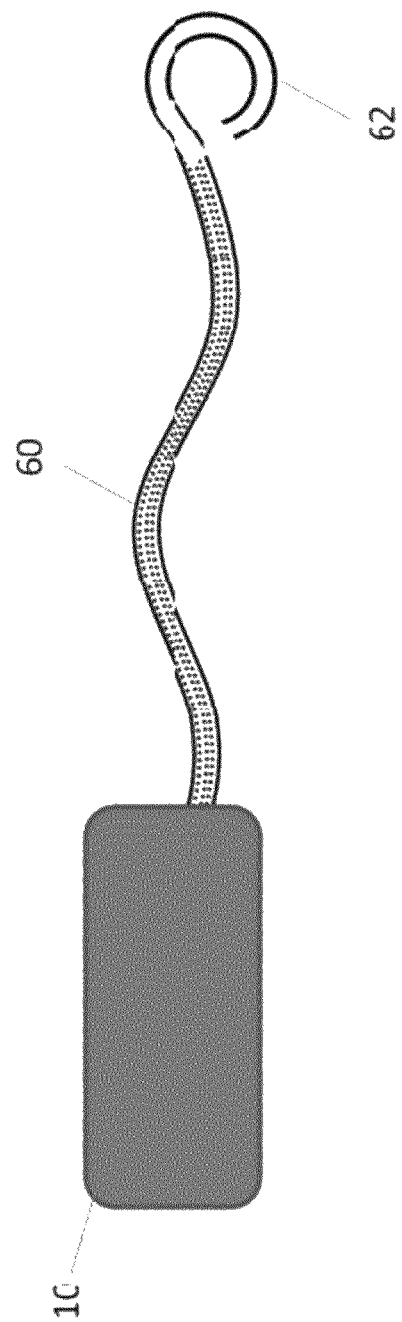

CONTINUOUS BLOOD GLUCOSE MONITOR

CROSS-REFERENCE TO RELATED APPLICATIONS

This application is a continuation of PCT International Application No. PCT/US2010/036950 filed on Jun. 1, 2010, which claims the benefit of priority to U.S. Prov. 61/217,537 filed Jun. 1, 2009 and 61/337,648 filed Feb. 11, 2010, each of which is incorporated herein by reference in its entirety.

FIELD OF THE INVENTION

The present invention relates to continuous biochemical monitoring systems. More specifically, the present invention relates to continuous glucose measuring devices which may be implanted within a subject and which detects or monitors glucose concentration from peritoneal fluid with minimal lag.

BACKGROUND OF THE INVENTION

Diabetes is a group of diseases characterized by high levels of blood glucose resulting from defects in insulin production, insulin action, or both. Diabetes is the leading cause of blindness in people ages 20 to 70 and is sixth leading cause of death in the United States. Overall, the risk for death among people with diabetes is about 2 times that of people without diabetes. The disease often leads to other complications such as kidney, nerve and heart disease and strokes. It is the leading cause for non-traumatic amputations and kidney failure.

Diabetes is reaching epidemic proportions in the United States. There are approximately 18.2 million people in the United States, or 6.3% of the population, who have diabetes. While an estimated 13 million have been diagnosed with diabetes, 5.2 million people (or nearly one-third) are unaware that they have the disease. Furthermore, diabetes is one of the most common chronic diseases in children and adolescents; about 151,000 people below the age of 20 years have diabetes.

Diabetics must diligently monitor the glucose level in their blood. Blood glucose levels should be maintained between 80 to 120 mg/dl before meals and between 100-140 mg/dl at bedtime. Self-monitoring of blood glucose (SMBG) permits diabetics to know what their blood sugar level is so they can adjust their food, insulin, or activity level accordingly. Improved glucose control can forestall, reduce, or even reverse some of the long-term complications of diabetes.

The gold standard for testing blood glucose is the measurement of glucose in a plasma sample obtained from a vein. A drop of blood is placed on a small window in a teststrip. Blood glucose acts as a reagent in a chemical reaction that produces a color change or generates electrons. The color change is detected by a reflectance-meter and reported as a glucose value. Alternatively, the electrons generated in the reaction are detected as an electrical current and reported as a glucose value.

Problems with existing SMBG devices include the requirement of a drop of blood for each test (normally acquired through a prick of the finger). The blood sampling can be painful and cause calluses to form. It also increases the risk for warts and infections. The acute discomfort associated with this presents the largest barrier to life-saving blood glucose control.

Minimally invasive technologies currently on the market in the United States include the GlucoWatch® Biographer and the Guardian® Continuous Glucose Monitoring System. The GlucoWatch® Biographer uses reverse iontophoresis, which involves applying an electrical microcurrent to the skin. The current pulls sodium through the intact skin, water follows sodium and water pulls glucose with it. The glucose concentration in this fluid is proportionate to the concentration in blood.

However, there are several problems with this technology. There is a lag time of 20 minutes before a blood glucose value can be reported. The concentration of glucose in the fluid is only 1/1,000 of glucose in the blood. A mild skin discomfort last for a few minutes when the device is first applied to the skin. The device is intended for use only by adults (age 18 and older) with diabetes. It is intended to supplement, not replace, standard home blood glucose monitoring devices. The user also has to calibrate the GlucoWatch® Biographer with a blood glucose value measured on a traditional, i.e. "fingerstick," monitor. Thus a standard (invasive) blood glucose monitor is still required.

The Guardian® Continuous Glucose Monitoring System is designed to automatically and frequently monitor glucose values in subcutaneous interstitial fluid (ISF). It measures ISF glucose every five minutes and it has a hypoglycemia alert. Once inserted, the sensor is virtually painless, but it requires entry of glucose readings from a standard monitor at least twice a day in order to calibrate the sensor. Furthermore, the readings from this monitor lag the actual blood glucose values by 15-20 minutes potentially resulting in over or under dosing of insulin.

Dexcom and Medtronic, among others, market a subcutaneously inserted CGM which functions for several days before requiring replacement. These devices, though, measure interstitial blood glucose which frequently lags blood glucose by 15 minutes or more. This lag alone is suboptimal (more manageable lag times are in the 5-10 minute range) and lag times may tend to be inconsistent. This means that there is no one control algorithm that can be used to create a closed-loop system since the inter- and intra-sensor variability in lag is too great (5-30 minutes according to recent reports) and doesn't apply to each sensor the same way or even apply to the same sensor during certain physiological situations. For the inter-sensor variability, a sensor is placed at least weekly in the subcutaneous space. During this weekly placement, one sensor may be tightly nestled in a capillary bed (lag time 5-10 min) while the sensor implanted a week later may instead be up against a muscle fiber or a region of fat (30 minute or greater lag time). Therefore a consistent control algorithm for both sensor placements without very poor control is difficult to use.

With respect to intra-sensor variability, there are many conditions which affect blood flow to the submucosa of the skin. Cold temperature, for example, will drastically impact blood flow to the skin. Another potential impact on blood flow is sleeping. There may be significant intra-sensor variability between sleeping and waking lag periods which may have resulted in the episodes of severe nocturnal hypoglycemia with closed loop control noted in the literature.

SUMMARY OF THE INVENTION

A system is provided which recognizes that the concentration of an analyte in blood is directly related to its concentration in peritoneal fluid (assuming it is not a large molecule). The present invention, then, provides for continuous blood glucose measurement in the peritoneal cavity (or blood stream itself) using a self-cleaning and sensing platform. The method and apparatus are particularly suited for continuously measuring blood glucose levels.

Generally, a device may be implanted subcutaneously with an attached catheter inserted within, e.g., the peritoneal cavity of a subject. Alternatively, the catheter and/or device may be inserted into another space, e.g., subcutaneous, vascular, peritoneal, cerebrospinal, pleural spaces, etc. The subcutaneous implant may also be placed in another cavity in order to simplify sensing. The peritoneal fluid which normally collects and/or flows through the peritoneal cavity may be detected by the catheter and analyzed via the device to detect the concentration of glucose within the fluid. The sensor, in one example, may comprise a lens and an emitter which sends out a signal at a predetermined frequency and wavelength as well as a detector which may receive the reflected wavelengths to determine the physiologic characteristics of the peritoneal fluid in proximity or in direct contact with the sensor.

In another variation, a sensor or lens may be cleaned by the intermittent release of a flow of fluid across the sensor/lens utilizing, e.g., an osmotic pump. This fluid may comprise a fluid dedicated for this purpose and stored within the device (or attached reservoir) or may serve another purpose (e.g., peritoneal insulin delivery fluid). This fluid may be pumped from its location within the device (or reservoir attached to the device) and may not require any active powering. A salt or other compound with osmotic activity and limited solubility in water may be stored in concentrated form (e.g., solid form) in a chamber within the device (or reservoir attached to the device). This reservoir may have an externally facing semipermeable membrane which allows water to flow into the reservoir based on the osmotic gradient established by the dissolving or solubilizing compound. Once the chamber fills to sufficient pressure, a controlled valve, check-valve, or other gate may open and allow for the pressurized fluid to course out of the chamber and activate the washing of the sensor or create mechanical action that may power the cleaning action of the sensor.

Active pump, mechanical, or energy delivery cleaning embodiments are envisioned as well which may be battery powered or inductively powered and/or recharged in order to provide the glucose sensing, insulin delivery and/or cleaning actions. In addition, while the medical field has been reluctant to utilize the peritoneal space for diagnostic and therapeutic purposes, the peritoneal space is a relatively protected space (with respect to preventing fibrosis and tissue reaction) and the concentration of analytes within the plasma are reflected to a lesser or greater degree (depending on molecular size) in the peritoneal fluid. The use of a peritoneal implant to allow for the chronic long-term monitoring of any analyte within the peritoneal fluid may accordingly be accomplished.

Information recorded by the implanted sensor and/or insulin pump may be transmitted wirelessly to an external unit capable of displaying this information. This information may also provide an indication that an intervention may be required. For example, a pressure sensor in line with the flush line may record the pressure and report that an increased pressure is required for the flush. This may trigger either more aggressive automatic flushing/cleaning or may result in the use of an external flush with or without active anti-clogging agents such as heparin, TPA, etc.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

FIGS. 5A to 5C show an example of the device of FIG. 4 utilizing the valve tipped catheter.

FIG. 6 shows an example of a device having a semi-permeable membrane embodiment with a curled tip catheter.

DETAILED DESCRIPTION OF THE INVENTION

Generally, a device may be implanted subcutaneously with an attached catheter inserted within, e.g., the peritoneal cavity of a subject. Alternatively, the catheter and/or device may be inserted into another space, e.g., subcutaneous, vascular, peritoneal, cerebrospinal, pleural spaces, etc. The subcutaneous implant may also be placed in another cavity in order to simplify sensing. The peritoneal fluid which normally collects and/or flows through the peritoneal cavity may be detected by the catheter and analyzed via the device to detect the concentration of glucose within the fluid.

The glucose sensor(s) may utilize any one of a variety of modalities including, but not limited to, enzymatic sensors, photometric sensors, mid-infrared and near-infrared wavelength sensors, phophorescent sensors, etc. More than one modality may be employed, as well, to ensure that results are accurate. The protective catheter and/or the sensor may also be replaced as needed or on a schedule. The subcutaneous implant may also be replaced if its battery requires renewal. These procedures may be conducted in a minimally invasive manner.

The device may also incorporate a sterilizing and/or cleaning mechanism as described in patent application PCT/US2008/73279 entitled "METHOD AND APPARATUS FOR AUTOMATED ACTIVE STERILIZATION OF FULLY IMPLANTED DEVICES" and U.S. Prov. 60/964,822 filed Aug. 15, 2007, each of which are herein incorporated by reference in their entirety.

Figure 1:
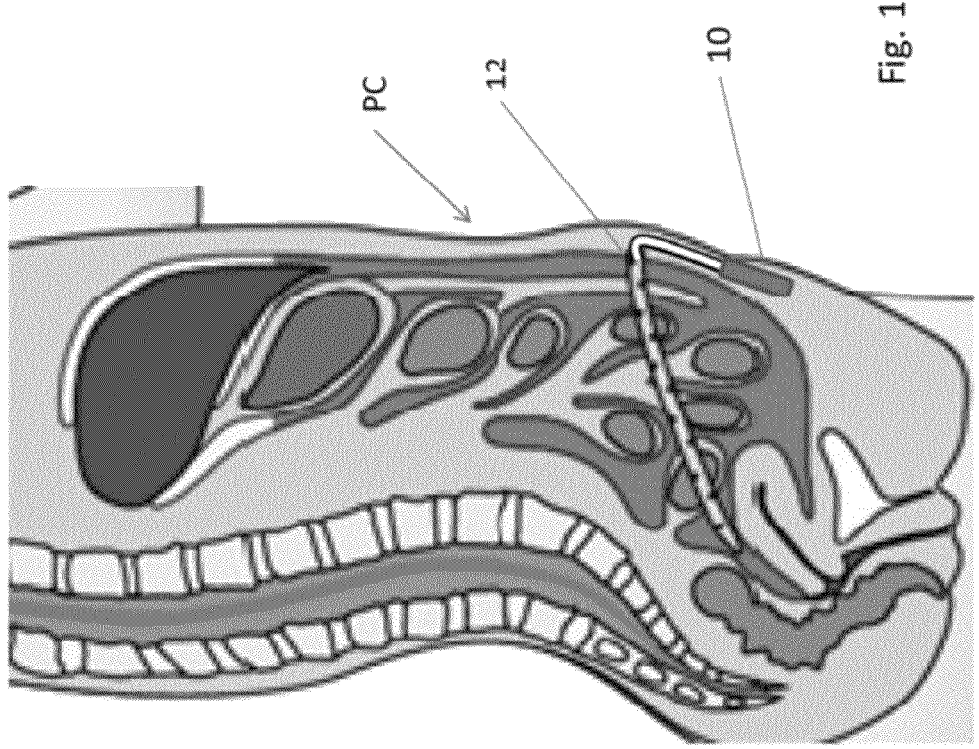
FIG. 1 illustrates an example for placement of the catheter-based embodiment of the device.

FIG. 1 illustrates one example for placement of the glucose sensing system within the peritoneal cavity PC of a subject. A glucose sensor assembly 10 may be implanted subcutaneously in proximity to the peritoneal cavity PC with a sensing catheter 12 attached to the assembly 10 and inserted directly into the peritoneal cavity PC and/or inserted into a difference space (e.g., subcutaneous, vascular, peritoneal, cerebrospinal, pleural spaces, etc.). The subcutaneous assembly 10 may also be placed in another cavity in order to simplify sensing. The assembly 10 may house a glucose sensor as well as the sensor/measurement electronics and an optional pump or actuator for pumping, e.g., insulin or some other fluid, as described in further detail herein. Optionally, the assembly 10 may also comprise an agitating mechanism and/or sensor clearing/cleaning mechanism. The protective catheter 12 may house the glucose sensor and may alternatively be positioned within, e.g., the pelvis, superior to the liver, etc. Additionally, a fluid reservoir may also be incorporated into the system for providing a fluid for back flushing the catheter 12 intermittently to maintain a clear flow channel.

Figure 2:
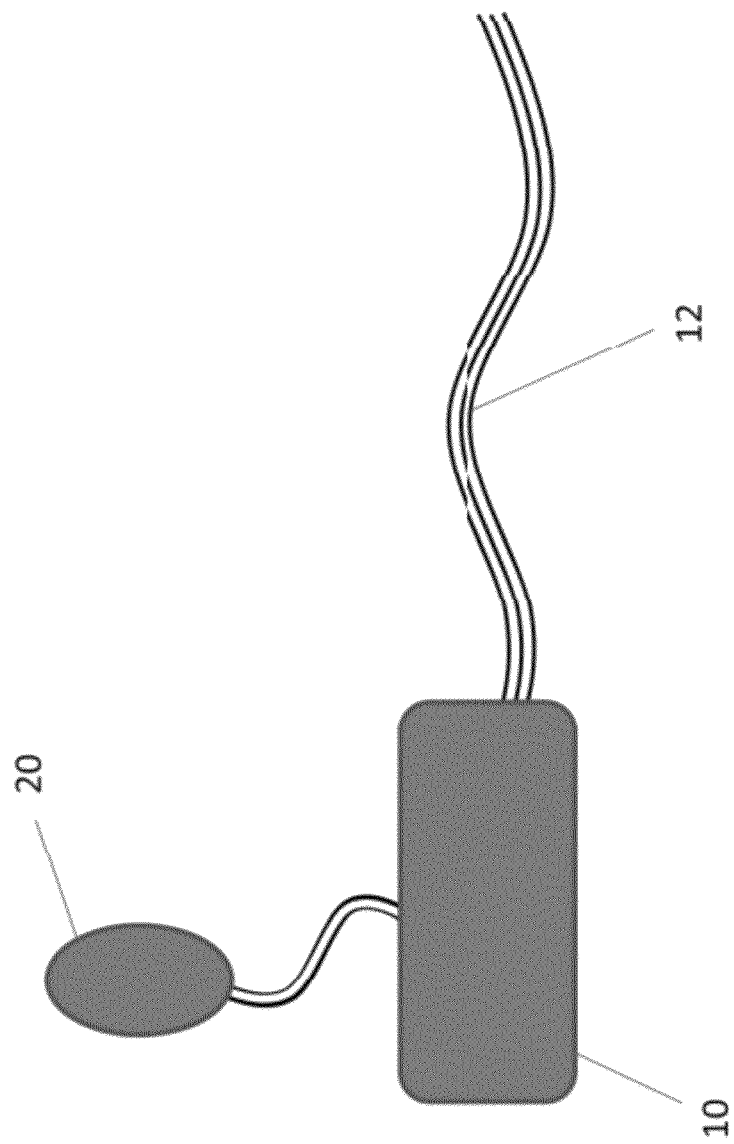
FIG. 2 shows an example of a fluid flow embodiment.

FIG. 2 illustrates an example of the system having the implantable assembly 10 with protective catheter 12 attached and extending therefrom. As the catheter 12 dwells within the peritoneal cavity PC, the peritoneal fluid may be drawn into the catheter 12 through one or more openings at the tip or along the length of the catheter 12 for measurement by a sensor within the system. The catheter 12 may protect the sensor housed within which may be surrounded by a non-debris forming fluid. For this reason, a fluid reservoir 20 (which may also be implanted within the subject) may be optionally attached in fluid communication with assembly 10 or integrated directly with assembly 10 for providing a circulating fluid for intermittently flushing the sensor as well as to clear the catheter line and/or to also ensure adequate exposure of fluid to the peritoneum. Additionally, fluid reservoir 20 may also provide for replenishment of the equilibration fluid which may be infused, allowed to equilibrate, measured for blood glucose then left in the cavity or withdrawn back into the reservoir. Optionally, one or more drugs or other active agents may be incorporated into fluid reservoir 20, e.g., to prevent clogging and/or preventing infection.

Figure 3:
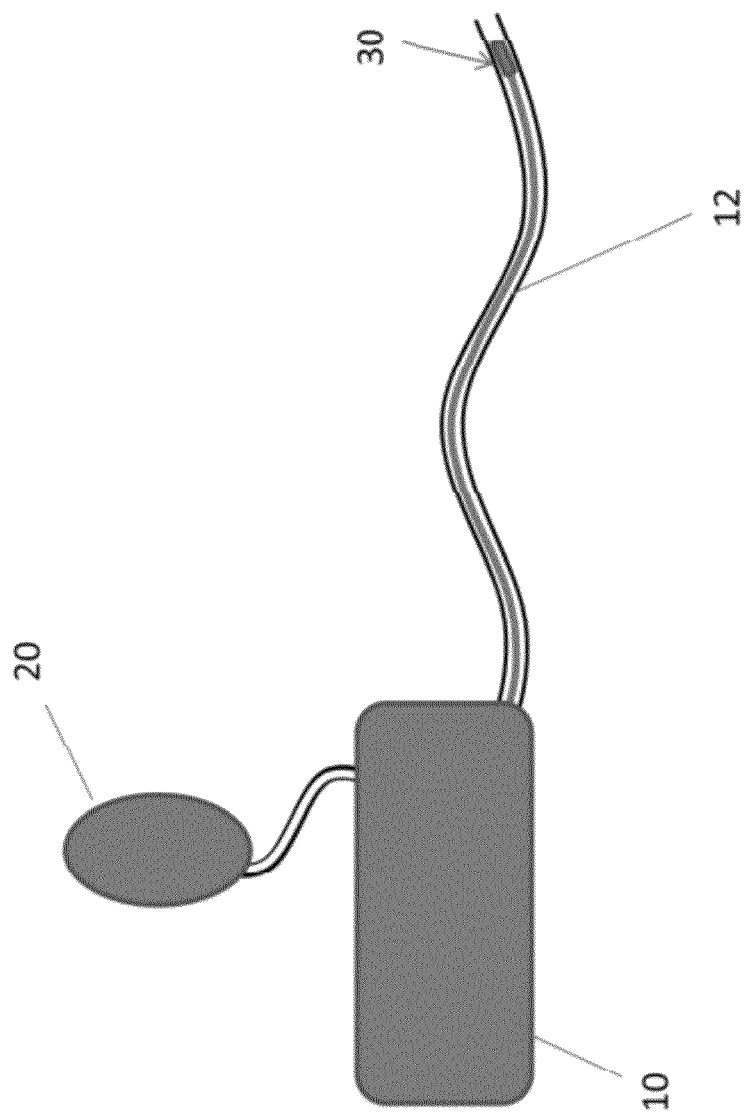
FIG. 3 shows an example of a sensor-cleaning catheter embodiment.

FIG. 3 illustrates a variation where a glucose sensor 30 (e.g., an optical sensor) may be positioned within the protective catheter 12. While the sensor 30 is in electrical communication with the assembly 10 through the catheter 12, sensor 30 may be positioned near or at a distal opening of the catheter 12. Thus, fluid may be circulated through the catheter 12 which may comprise a dual-lumen or single lumen catheter which allows for intermittent flow (e.g., in then out) of fluid drawn in over the sensor 30 and within an optional pump within assembly 10. Such a pump may urge fluid through the catheter 12 to clean the sensor 30 or catheter 12 via direct mechanical removal of any film or ultrasound/agitation. The pump may be configured to intermittently reverse direction to ensure lumen patency. The sensor 30, in one example, may comprise a lens and an emitter which sends out a signal at a predetermined frequency and wavelength as well as a detector which may receive the reflected wavelengths to determine the physiologic characteristics of the peritoneal fluid in proximity or in direct contact with the sensor 30.

Additionally and/or alternatively, the sensor 30 may be moved relative to the assembly 10 and/or catheter 12 (e.g., slide out of the assembly 10 and/or catheter 12 or rotate within the assembly 10 or catheter 12. The catheter 12 may alternatively remain stationary its position and instead be cleaned using ultrasound, fluid lavage, etc. In this and other embodiments, one or more flushing ports or reservoirs may be incorporated to provide for cleaning of the system in the event that the system is not in direct contact with the fluid it needs to take its readings.

The optional reservoir 20 may be intermittently pumped (or on demand) by assembly 10 to clear catheter 12 lumen, e.g., by flushing or back-flushing the fluid through the catheter 12. Moreover, each of the variations described herein may be optionally inductively recharged and/or refilled with backflush fluid (or insulin if full artificial pancreas). Furthermore, assembly 10 may also integrate wireless capabilities for providing external communication to transmit data from the glucose sensor 30 to, e.g., an external reader, an insulin pump, etc.

Figure 4:
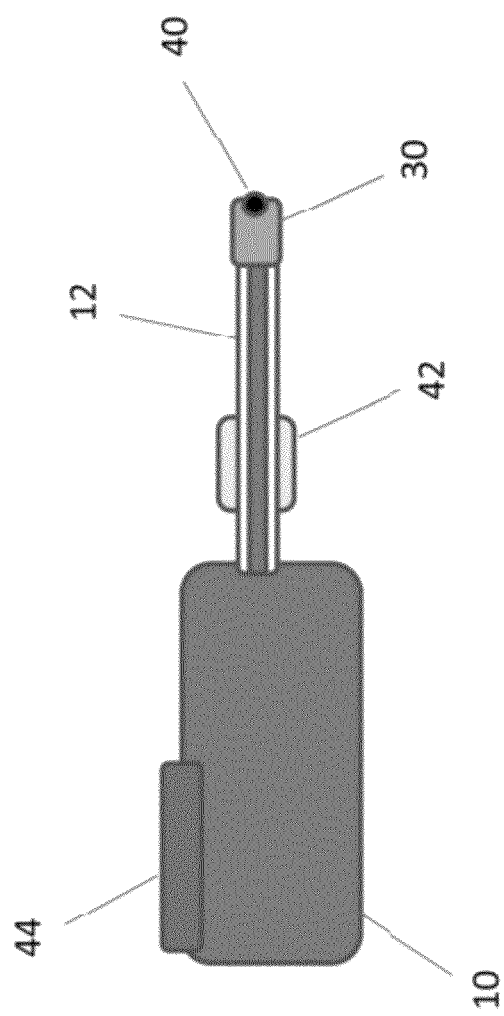
FIG. 4 shows an example incorporating a valve-tipped catheter with sensor movement past this cleaning valve for taking measurements.

FIG. 4 illustrates another variation showing protective catheter 12 having a cleaning tip 40 (shown here as a silicone tip) which may function as a valve or window which cleans the sensor 30 in vivo within catheter 12 as it slides or moves past the tip 40. Accordingly, the sensor may be urged to shift or move via an active mechanism housed within assembly 10. The sensor 30 may then return to its resting position between readings where it is protected by the catheter 12 housing. Alternatively, the sensor 30 may be exposed by default and drawn into the catheter 12 only intermittently on a programmed basis or when it senses interference by debris, etc. In the event that the sensor 30 protrudes from the catheter 12, the tip of the sensor 30 may be blunt and atraumatic so as to prevent damage to surrounding tissue. If placed in the peritoneal cavity PC, the device may be positioned such that the end of the catheter 12 is in the pelvis and away from the omentum and/or mesentery. If omentum is seen during or prior to placement of a peritoneal sensor, an omentectomy may be performed to improve device reliability.

Additionally, one or more in-growth cuffs 42 may be placed upon or along the catheter 12 outer surface, as shown, to prevent tracking of any infection or fluid between the sensing catheter 12 (which may be in the subcutaneous, vascular, peritoneal, cerebrospinal or, pleural cavities, etc.) and the assembly 10. Moreover, one or more optional flushing port 44 may be integrated along the assembly 10 to facilitate the cleaning of a clogged catheter 12.

FIGS. 5A to 5C illustrate an example of how the tip 40 may be utilized for cleaning or clearing the sensor 30. As shown in FIG. 5A, sensor 30 may be contained within catheter 12 and proximal to tip 40. A blunt tip 50 of sensor 30 may be urged distally such that it is forced through valve tip 40, as shown in FIG. 5B, thereby cleaning the surface of the sensor 30 and allowing for the exposed sensor 30 to take a reading of the peritoneal fluid in proximity to the catheter 12. If valve 40 or catheter 12 are occluded, a flushing port may be used as well. Once the reading has been taken, sensor 30 may then retract proximally into catheter 12 past tip 40 which may again clean sensor 30, as shown in FIG. 5C. An inductive recharging coil 52 is also shown in this variation within assembly 10 for enabling the inductive charging of the device.

FIG. 6 illustrates another variation of a device utilizing a semi-permeable membrane 60 along the catheter body and a curled, non-erosive tip 62. The semi-permeable membrane 60 may allow for long-term analyte diffusion through the membrane 60 and into the catheter for contact with the sensor 30 housed within without foreign body reaction or requirement for fluid infusion. The membrane 60 may allow for rapid diffusion utilizing, e.g., ePTFE, silicone lattice, etc. or coatings such as albumin, heparin, etc.

The optional curled tip 62 of the catheter may prevent erosion within the body cavity. This tip 62 may be tunneled to the site of implantation. Placement in the peritoneal cavity may involve dissection of the posterior rectus sheath from the peritoneum, angulation of the catheter downward into the true pelvis then perforation of the peritoneum to ensure downward angulation of the catheter into the pelvis. Proximal catheter may then be tunneled subcutaneously to the subcutaneous portion of the implant. In yet another embodiment, the distal end of the peritoneal catheter may be inserted into the peritoneal cavity then the tip of the catheter may be firmly attached to the parietal peritoneum or bladder with the sensor located proximal to the attached tip within the peritoneal cavity. The tip of the catheter may also exit the peritoneal cavity and be buried in the subcutaneous space leaving both ends of the catheter in the subcutaneous space with a short segment containing the sensor and/or infusion port exposed within the peritoneal cavity. This feature may prevent potential erosion of the tip of the catheter through visceral peritoneum into peritoneal structures and will maintain the catheter segment firmly and permanently away from the omentum and/mesentery. This type of catheter placement may be useful for any peritoneal catheter including peritoneal dialysis catheters to prevent complications and obstructions. If placed with laparoscopy, open surgery or percutaneously the omentum may also be tacked up away from the catheter, as necessary, during placement. The catheter may be placed with ultrasound visualization, laparoscopic visualization, other radiologic guidance and/or without visualization.

This and the other embodiments may also benefit from an inductive powering or charging circuit. In order to minimize the size of the implant and maximize its life, a small battery may be used that requires recharging on a daily, weekly or monthly basis. Alternatively, the device may be externally powered by placement of an inductive coil over the device during operation, as shown above. Any of the features illustrated in any of the figures or described within this specification may be used alone or in conjunction with other features illustrated in each figure.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A method of determining a physiologic parameter within a body cavity, comprising:
   implanting a sensor assembly subcutaneously and a catheter within a peritoneal cavity of a subject, wherein the catheter is coupled to the assembly and includes a sensor at the distal end of the catheter;
   drawing a peritoneal fluid from within the peritoneal cavity into the catheter and in fluid contact with the sensor;
   sensing the peritoneal fluid with the sensor;
   determining, a concentration of an analyte from the peritoneal fluid with a detector programmed to receive a signal from the sensor; and
   flushing the sensor periodically with fluid introduced through the catheter.

2. The method of claim 1 wherein the fluid is drawn from within the peritoneal cavity.

3. The method of claim 1 wherein determining comprises determining a concentration of glucose from the peritoneal fluid.

4. The method of claim 1 further comprising clearing the sensor in vivo via a valve tip.

5. The method of claim 4 wherein clearing, comprises actuating the sensor to move relative to the valve tip thereby clearing the sensor.

6. The method of claim 1 wherein flushing comprises flushing the sensor with the fluid from a fluid reservoir in fluid communication with the catheter.

7. The method of claim 6 wherein the fluid reservoir is implanted in the subject.

8. The method of claim 1 further comprising infusing a therapeutic fluid into the subject based upon the concentration of the analyte.

9. The method of claim 1 wherein the peritoneal fluid is drawn into the catheter using a pump.

10. A method of treating a patient with insulin, comprising:
    implanting a catheter having a sensor within a peritoneal cavity of a subject, wherein the sensor is at the distal end of the catheter;
    drawing a peritoneal fluid from within the peritoneal cavity into the catheter and in fluid contact with the sensor;
    sensing the peritoneal fluid with the sensor;
    determining a concentration of glucose from the peritoneal fluid with a detector programmed to receive a signal from the sensor;
    infusing insulin into the peritoneal cavity based upon the concentration of glucose; and
    flushing the sensor periodically with fluid introduced through the catheter.

11. The method of claim 10 wherein implanting comprises placing a sensing assembly subcutaneously within the subject, where the sensing assembly is coupled to the catheter.

12. The method of claim 10 further comprising clearing the sensor in vivo via a valve tip.

13. The method of claim 12 wherein clearing comprises actuating the sensor to move relative to the valve tip thereby clearing the sensor.

14. The method of claim 10 further comprising flushing the sensor with the fluid from a fluid reservoir in fluid communication with the catheter.

15. The method of claim 14 wherein the fluid reservoir is implanted in the subject.

16. The method of claim 10 wherein the peritoneal fluid is drawn into the catheter using a pump.

17. The method of claim 10 wherein the fluid is drawn from within the peritoneal cavity.

18. A method of determining a physiologic parameter within a body cavity, comprising:
    implanting a sensor assembly subcutaneously and a catheter within a peritoneal cavity of a subject, wherein a sensor is at the distal end of the catheter;
    infusing a semipermeable membrane of the catheter with peritoneal fluid from within the peritoneal cavity wherein the peritoneal fluid comprises an analyte;
    determining a concentration of the analyte diffused through the semipermeable membrane with a detector programmed to receive a signal from the sensor; and
    flushing the sensor periodically with fluid introduced through the catheter.

19. The method of claim 18 wherein the fluid is drawn from within the peritoneal cavity.

20. The method of claim 18 wherein determining comprises determining a concentration of glucose from the peritoneal fluid.

21. The method of claim 18 further comprising clearing the sensor in vivo via a valve tip.

22. The method of claim 21 wherein clearing comprises actuating the sensor to move relative to the valve tip thereby clearing the sensor.

23. The method of claim 18 further comprising flushing the sensor with the fluid from a fluid reservoir in fluid communication with the catheter.

24. The method of claim 23 wherein the fluid reservoir is implanted in the subject.

25. The method of claim 18 further comprising infusing insulin into the subject based upon the concentration of the analyte.

* * * * *